United States Patent
Bradbury

(10) Patent No.: US 8,420,794 B2
(45) Date of Patent: Apr. 16, 2013

(54) ANTI-INFLUENZA M2E ANTIBODY

(75) Inventor: Andrew M. Bradbury, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 13/296,414

(22) Filed: Nov. 15, 2011

(65) Prior Publication Data

US 2012/0064085 A1 Mar. 15, 2012

Related U.S. Application Data

(62) Division of application No. 12/592,241, filed on Nov. 20, 2009, now Pat. No. 8,080,244.

(60) Provisional application No. 61/199,891, filed on Nov. 21, 2008.

(51) Int. Cl.
*C07H 21/02* (2006.01)
*C07K 14/00* (2006.01)
*A61K 39/395* (2006.01)

(52) U.S. Cl.
USPC ........................ 536/23.1; 530/350; 424/130.1

(58) Field of Classification Search ........................ None
See application file for complete search history.

(56) References Cited

U.S. PATENT DOCUMENTS

2005/0170334 A1 8/2005 Mikayama et al.
2009/0162366 A1 6/2009 Mikayama et al.

OTHER PUBLICATIONS

Zhang et al. Molecular Immunology, 2006, vol. 43, p. 2195-2206.*
Delagrave et al., "Effects of Humanization by Variable Domain Resurfacing on the Antiviral Activity of a Single-Chain Antibody against Respiratory Syncytial Virus," *Protein Eng.*, vol. 12:357-362, 1999.
Di Niro et al., "Construction of Miniantibodies for the In Vivo Study of Human Autoimmune Diseases in Animal Models," *BMC Biotech.*, vol. 7:1-10, 2007.
Zhang et al., "Fine Specificity and Sequence of Antibodies Directed against the Ectodomain of Matrix Protein 2 of Influenza A Virus," *Mol. Immuno.*, vol. 43:2195-2206, 2006.

* cited by examiner

*Primary Examiner* — Agnieszka Boesen
(74) *Attorney, Agent, or Firm* — Klarquist Sparkman, LLP

(57) ABSTRACT

Humanized recombinant and monoclonal antibodies specific for the ectodomain of the influenza virus M2 ion channel protein are disclosed. The antibodies of the invention have anti-viral activity and may be useful as anti-viral therapeutics and/or prophylactic/vaccine agents for inhibiting influenza virus replication and for treating individuals infected with influenza.

10 Claims, 5 Drawing Sheets

Fig.4: ELISA based recognition of M2 on cell surfaces

SEQUENCE LISTING

```
<160> NUMBER OF SEQ ID NOS: 7

<210> SEQ ID NO 1
<211> LENGTH: 113
<212> TYPE: PRT
<213> ORGANISM: Artificial Sequence
<220> FEATURE:
<223> OTHER INFORMATION: Polypeptide encoded by synthetic DNA encoding
      variable light chain of recombinant antibody

<400> SEQUENCE: 1

Asp Ile Val Met Thr Gln Ser Pro Asp Ser Leu Ala Val Ser Leu Gly
1               5                   10                  15

Glu Arg Ala Thr Met Asn Cys Lys Ser Ser Gln Arg Leu Leu Tyr Ser
            20                  25                  30

Ser Asp Gln Lys Asn Tyr Leu Ala Trp Tyr Gln Gln Lys Pro Gly Gln
        35                  40                  45

Pro Pro Lys Val Leu Ile Tyr Trp Ala Ser Thr Arg Val Ser Gly Val
    50                  55                  60

Pro Asp Arg Phe Ser Gly Ser Glu Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Tyr Pro Leu Thr Phe Gly Gln Gly Thr Lys Val Glu Ile
            100                 105                 110

Lys
```

<210> SEQ ID NO 2
<211> LENGTH: 119
<212> TYPE: PRT
<213> ORGANISM: Artificial Sequence
<220> FEATURE:
<223> OTHER INFORMATION: Polypeptide encoded by synthetic DNA encoding
      variable heavy chain of recombinant antibody

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Gly Leu Glu Trp Ile
        35                  40                  45

Gly Val Ile Ser Thr Tyr Thr Gly Lys Thr Asn Tyr Ser Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Gly Asp Tyr Asp Ala Trp Phe Ala Tyr Trp Gly Gln Gly
            100                 105                 110

Thr Leu Val Thr Val Ser Ser
        115

<210> SEQ ID NO 3
<211> LENGTH: 339
<212> TYPE: DNA
<213> ORGANISM: Artificial Sequence
<220> FEATURE:
<223> OTHER INFORMATION: Synthetic DNA encoding variable light chain of
      recombinant antibody

<400> SEQUENCE: 3
gacatcgtta tgacacaaag cccagacagc ctggccgtga gtctggggga gcgtgccaca      60
atgaactgca agagtagcca gcgcctgctg tattcctcag accaaaaaaa ctatctggcg     120
tggtatcagc agaaaccagg ccagccccccg aaagtcctca tctactgggc agcactcgc     180 gtttcaggtg tgcccgatcg cttcagcggc agcgagagtg gcaccgattt cacgctgacg     240
atctccagcc tgcaagcgga ggacgttgcg gtctactatt gccagcagta ttatacttac     300
cctcttactt ttggtcaggg caccaaagtt gaaattaaa                            339

<210> SEQ ID NO 4
<211> LENGTH: 357
<212> TYPE: DNA
<213> ORGANISM: Artificial Sequence
<220> FEATURE:
<223> OTHER INFORMATION: Synthetic DNA encoding variable light chain of
      recombinant antibody

<400> SEQUENCE: 4
caggttcaac tggtgcagtc cggggcggaa gtgaaaaagc cgggtgctag tgtgaaagtc      60
agctgcaaag ccagcggtta tacgtttacc gattacgcca tgcattgggt gcggcaggcc     120
cccggccaag gccttgaatg gatcggtgtt attagcactt acaccggtaa aacgaattac     180
agccagaagt ttaagggccg cgcaactatg accgtggata atctatctc taccgcatat     240 atggaactgt ctcgcctgcg cagcgatgac acggctgtgt attactgcgc ccgccgcgga     300

```
gactacgatg catggtttgc ttattggggg cagggtactc tggttaccgt atctagt         357
```

<210> SEQ ID NO 5
<211> LENGTH: 24
<212> TYPE: PRT
<213> ORGANISM: Artificial Sequence
<220> FEATURE:
<223> OTHER INFORMATION: Influenza A virus M2e consensus sequence

<400> SEQUENCE: 5

Met Ser Leu Leu Thr Glu Val Glu Thr Pro Ile Arg Asn Glu Trp Gly
1               5                   10                  15

Cys Arg Cys Asn Asp Ser Ser Asp
            20

<210> SEQ ID NO 6
<211> LENGTH: 119
<212> TYPE: PRT
<213> ORGANISM: Artificial Sequence
<220> FEATURE:
<223> OTHER INFORMATION: Variable heavy chain sequence of 14C2

<400> SEQUENCE: 6

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Ile Phe Thr Asp Tyr
            20                  25                  30

Ala Met His Trp Val Lys Gln Ser His Ala Lys Ser Leu Glu Trp Ile
        35                  40                  45

Gly Val Ile Ser Thr Tyr Thr Gly Lys Thr Asn Tyr Ser Gln Lys Phe
    50                  55                  60

Lys Gly Lys Ala Thr Met Thr Val Asp Lys Ser Ser Thr Ala Tyr
65                  70                  75                  80

Met Glu Leu Ala Arg Leu Thr Ser Glu Asp Ser Ser Val Tyr Tyr Cys
                85                  90                  95

Ala Arg Arg Gly Asp Tyr Asp Ala Trp Phe Ala Tyr Trp Gly Gln Gly
            100                 105                 110

Thr Leu Val Thr Val Ser Ala
        115

<210> SEQ ID NO 7
<211> LENGTH: 113
<212> TYPE: PRT
<213> ORGANISM: Artificial Sequence
<220> FEATURE:
<223> OTHER INFORMATION: Variable light chain sequence of 14C2

<400> SEQUENCE: 7

Asp Ile Val Met Ser Gln Ser Pro Ser Ser Leu Ala Val Ser Val Gly
1               5                   10                  15

Glu Lys Val Ser Met Thr Cys Lys Ser Ser Gln Arg Leu Leu Tyr Ser
            20                  25                  30

Ser Asp Gln Lys Asn Tyr Leu Ala Trp Tyr Gln Gln Lys Pro Gly Gln
        35                  40                  45

Ser Pro Lys Val Leu Ile Tyr Trp Ala Ser Thr Arg Val Ser Gly Val
    50                  55                  60

Pro Asp Arg Phe Thr Gly Ser Glu Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

-continued

```
Tyr Tyr Thr Tyr Pro Leu Thr Phe Gly Ala Gly Thr Lys Leu Glu Leu
            100                 105                 110
Lys
```

ANTI-INFLUENZA M2E ANTIBODY

CROSS REFERENCE TO RELATED APPLICATIONS

This is a divisional of U.S. application Ser. No. 12/592,241, filed Nov. 20, 2009, issued as U.S. Pat. No. 8,080,244 on Dec. 20, 2011, which claims the benefit of U.S. Provisional Application Ser. No. 61/199,891, filed Nov. 21, 2008, both of which are herein incorporated by reference in their entirety.

STATEMENT AS TO RIGHTS TO INVENTIONS MADE UNDER FEDERALLY SPONSORED RESEARCH OR DEVELOPMENT

This invention was made with government support under Contract No. DE-AC52-06 NA 25396 awarded by the U.S. Department of Energy. The government has certain rights in the invention.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Nov. 10, 2011, 6.39 KB, which is incorporated by reference herein.

BACKGROUND OF THE INVENTION

Influenza viruses cause a highly contagious acute respiratory disease that has been responsible for epidemic and pandemic disease in humans for centuries. In the 20$^{th}$ century, influenza claimed millions of human lives in three different pandemics, i.e., 40 million worldwide deaths during the Spanish flu by the influenza strain H1N1 in 1918, 70,000 American deaths in 1957 by the influenza H2N2 strain, and 34,000 American deaths in 1968 by the influenza H3N2 strain. Currently, 5-20% of the United States population contract influenza annually, and more than 200,000 people become hospitalized as a result of complications, with approximately 36,000 mortalities per year (Fiore et al., 2008, Hoyert et al., 2005, Podewils et al., 2005). Depending on the antigen differences in nucleoprotein (NP) and matrix protein (M), influenza viruses are divided into three major subtypes, A, B and C.

Influenza A viruses are the major causes of human flu epidemics. Influenza A is subject to regular antigenic changes, brought about either by genetic drift and inter-type gene re-assortment (genetic shift). In both situations, prior immunity to influenza does not necessarily prevent infection with the new type, leading to localized epidemics or, in the case of genetic shift, a global pandemic of influenza. Influenza A is also responsible for all Avian flu.

Vaccines are the mainstay of prophylaxis against influenza, but there are significant technical and safety issues attendant to vaccines, including difficulties in predicting which viral strains may emerge, preparing sufficient quantities of vaccine, poor immunogenicity in the elderly and very young, and difficulty in storage and administration.

Influenza anti-viral drugs are an important adjunct to vaccination; however, substantial drug resistance has developed in influenza strains to two of the four currently approved anti-viral drugs (Hayden and Hay, 1992). Furthermore, only two anti-viral drugs (rimantadine and oseltamivir) are approved for chemoprophylaxis of influenza virus infection (Govorkova et al., 2001). The evidence for viral resistance to anti-viral agents indicates that more than one drug is necessary to effectively combat influenza. As a consequence of these persistent difficulties, new therapeutic and vaccine approaches for influenza are earnestly sought. In particular, the concept of a "universal vaccine" has generated much interest.

The M gene of influenza A encodes two proteins in overlapping frames: M1, the capsid protein and M2, an ion channel protein. Both M1 and M2 are highly conserved, with M2 encoding a small ectodomain (M2e) (Palese, 2006), making it a potential target for antibody-based immunity. The ability of a monoclonal anti-M2e antibody to reduce viral replication (Zebedee and Lamb, 1988) suggested M2e as a potential vaccine target. Slepushkin et al. demonstrated protection following M2e vaccination using baculovirus-expressed protein, with serum antibody responses detected against both amino- and carboxy-terminal M2e peptides, and presumed to be responsible for the protection against lethal challenge with a matched (H2N2) influenza A virus (Slepushkin et al., 1995). In 1999, Neirynck et al. described a "universal vaccine" based upon the 23 a.a. ectodomain of M2 and demonstrated protection against H3N2 challenge virus with an M2e sequence identical to or differing by one amino acid from the vaccine constructs (Neirynck et al., 1999). Multiple antigenic peptide (MAP) vaccines have also been shown to be protective (Mozdzanowska et al., 2003).

While most human H1 and H3 influenza viruses share complete homology with the M2e consensus sequence (termed "conM2" herein), M2e-specific antibodies have not been shown to bind to M2e peptides with considerable sequence divergence. In a study of M2e-carrier conjugate vaccines, serum antibodies specific for conM2 or the M2e sequence of A/PR/8/34 (A/PR8, H1N1) did not cross-react with M2e peptides from H5 and H7 avian viruses having 3 or 4 mismatches out of 24 a.a. (Fan et al., 2004). In another study, immunization with plasmid containing the entire M gene from A/PR8 was shown to protect against matched (H1N1) challenge, however there was limited evidence for M2-specific immune responses (Okuda et al., 2001, Watabe et al., 2001). Importantly, while a recent study used matched M2e peptide-liposome vaccines of various subtypes (Ernst et al.), none of the previously published work has documented protection against challenge with influenza viruses across substantial M2e sequence differences from the immunizing antigen and specifically against potential pandemic H5N1 influenza challenge. In contrast, we have obtained evidence that M2-specific antibody responses can potentially be broadly cross-reactive and protect against divergent influenza virus challenge (Tompkins et al., 2007). While vaccines based on M2 may become very useful, it is also possible that human or humanized antibodies recognizing M2 may be effective as passive vaccines or therapeutics.

The sequences of six murine anti-M2e mAbs, generated either by consecutive pulmonary infection (Mozdzanowska, et al., 2003) or immunization with purified M2 (Zebedee and Lamb, 1988), have recently been published (Zhang et al., 2006). These all have very similar recognition properties, with the recognized epitope located between amino acids 4-16 of the external portion of M2 (Zhang, et al., 2006). Interestingly, these mAbs all use the same VH, DH and JH genes, with minor differences (less than 7%) between them, and only two different kappa light chains. One of these antibodies, 14C2, recognizes M2e when expressed on the cell membrane after infection (Zebedee and Lamb, 1988), and reduces viral plaque size (Zebedee and Lamb, 1988) and viral production levels (Hughey et al., 1995) in vitro. Both 14C2 and another antibody, M2-80, have also been shown to have significant protective effects in mice (Mozdzanowska et al., 1999, Treanor et al., 1990, Zharikova et al., 2005).

The demonstrated anti-viral activity of 14C2 suggests that it would be a good candidate for humanization (Carter et al., 1992, Chothia et al., 1985, Hwang et al., 2005, Kettleborough et al., 1991, Pedersen et al., 1994, Roguska et al., 1994, Routledge et al., 1991, Studnicka et al., 1994, Tsurushita et al., 2005, Vargas-Madrazo and Paz-Garcia, 2003), a term describing a series of techniques in which the sequence of a murine antibody is changed so that it more closely resembles a human antibody sequence. Conceptually, this involves taking the binding loops of the murine antibody and grafting them onto a human variable region framework in such a way that they are still able to recognize the antigen of interest. This often involves the retention of some critical murine framework amino acids required to maintain the correct orientation of the binding site loops, as well as subsequent mutation and selection to maintain affinity. Humanization has been widely used, and nine approved drugs are humanized antibodies. Although a number of different methods to carry out humanization have been developed (Carter, et al., 1992, Chothia, et al., 1985, Hwang, et al., 2005, Kettleborough, et al., 1991, Pedersen, et al., 1994, Roguska, et al., 1994, Routledge, et al., 1991, Studnicka, et al., 1994, Tsurushita, et al., 2005, Vargas-Madrazo and Paz-Garcia, 2003), none of them has been demonstrated to be significantly superior to any other. Here we describe the humanization of the M2e-specific murine mAb, 14C2, demonstrate specificity for the native M2 protein, and confirm anti-viral activity of the humanized single-chain minibodies.

Antibodies provide an appealing strategy for the prevention or treatment of viral infections. Their specificity, relatively long half-life and limited toxicity are just a few of the strengths of this therapeutic modality. Although polyclonal antibodies are FDA approved for eight pathogens (hepatitis B, CMV, botulism, RSV, rabies, tetanus, VZV and vaccinia) (Zeitlin et al., 2000), there is a clear preference for therapeutics that are better defined. There were initial hopes that rodent mAbs could be used in therapy, but their immunogenicity has led to efforts to create mAbs which are more human in their sequences. With the advent of modern molecular biology, three main classes of mAbs with lower immunogenicity have been developed. These include chimeric antibodies, in which murine V regions are fused to human constant regions (Morrison et al., 1984), humanized antibodies, in which murine antigen binding loops are grafted onto human variable region framework sequences (Jones et al., 1986), and fully human antibodies, the latter being made by phage display (reviewed in Winter et al., 1994), or by applying traditional hybridoma technology to mice transgenic for the human immunoglobulin loci (reviewed in Lonberg, 2005). As chimeric antibodies retain some residual immunogenicity, humanized and human antibodies are most frequently used and are equally represented in clinical trials and approved drugs (Reichert et al., 2005).

Recombinant antibodies offer many advantages for the treatment of diseases (Reichert, et al., 2005), including those caused by infectious agents (Reichert and Dewitz, 2006), and viruses in particular (Marasco and Sui, 2007). Compared to antibodies produced in animals, they have greater potency, defined activity, lack infectious agents, avoid the development of serum sickness caused by immune responses to non-human antibodies, and with a half-life of up to 4 weeks, provide long periods of protection with relatively infrequent dosage schedules. For all indications, eighteen mAbs have received regulatory approval and over 150 are now in clinical development (Reichert and Dewitz, 2006, Reichert, et al., 2005). One mAb against respiratory syncytial virus, providing significant reduction in morbidity, has been approved for treatment of high risk pediatric cases and mAbs against over twenty other infectious agents, including SARS, rabies, West Nile virus, HIV, Dengue, Ebola, Hepatitis A, B and C, anthrax, E. coli and Staphylococcus, are under development (Marasco and Sui, 2007, Reichert and Dewitz, 2006). In addition to their therapeutic value, antibodies also have potential as passive vaccines, which can translate into months of protection following prophylactic administration: long enough to cover a flu season, or the community duration of a pandemic (Bartlett, 2006). As the means of production of human mAbs are well known, the process of manufacturing, as well as the necessary toxicology and clinical safety testing requirements are well understood. This results in a rapid development timeline, once suitable candidates have been identified. This is especially true for antibodies recognizing infectious epitopes, rather than human proteins, in which inadvertent unexpected reactions may occur (Feldman et al., 2000).

Influenza provides a number of viral targets for antibody therapies (Beigel and Bray, 2008). Antibodies to the hemagglutinin can neutralize the virus and readily prevent infection, however these antibodies are subtype and in many cases strain or Glade specific and so have limited use as antibody therapies (Simmons et al., 2007), even though the efficacy of the annual vaccines is related to their ability to induce HA antibodies. Neuraminidase antibodies, while not neutralizing may also protect against infection (Gillim-Ross and Subbarao, 2007). Unexpectedly, antibodies against the influenza nucleoprotein (NP), which coats the viral RNA have also been shown to be protective in mice (Carragher et al., 2008), although previous studies suggest NP immunization protects via T and not B cell responses (Epstein, 2003, Ulmer et al., 1993). Finally, the M2 protein has been widely explored as a target for both vaccines and drug therapies. M2 is an appealing target as it is expressed to high levels on virus-infected cells, it is relatively conserved compared to other surface viral antigens, and antibody responses to M2 proteins have been demonstrated to protect against human and avian influenza virus infections (Fiers et al., 2004, Tompkins, et al., 2007, Tripp and Tompkins, 2008, Wang et al., 2008). M2e, the M2 ectodomain is conserved at least in part because it is generated as a spliced transcript and the first 9 amino acids are shared by M1 capsid and M2 pore proteins (Palese, 2006).

SUMMARY OF THE INVENTION

The invention provides humanized recombinant and monoclonal antibodies specific for the ectodomain of the influenza virus M2 ion channel protein with anti-viral activity. The anti-M2e antibodies of the invention may be useful as anti-viral therapeutics and/or prophylactic/vaccine agents for inhibiting influenza virus replication and for treating individuals infected with influenza. Also provided are methods for the production of the antibodies of the invention.

In one embodiment, the invention provides an isolated anti-M2e monoclonal antibody which is specific for influenza M2e polypeptide, and which comprises a light chain variable region having the amino acid sequence of SEQ ID NO: 1 and a heavy chain variable region having the amino acid sequence of SEQ ID NO: 2. In other embodiments, the invention provides various fragments and derivatives thereof, such as single chain Fv (scFv), Fab or Fab', minibody and the like. Full length immunoglobulin molecules are also included, and may be selected from the classes consisting of IgA, IgD, IgE, IgG and IgM.

Further, the invention provides an antibody formulation comprising an anti-M2e antibody of the invention and a pharmaceutically acceptable carrier. In view of the demonstrated anti-viral activity of the M2e antibodies of the invention (see Example 1, infra), the invention also provides methods of treating individuals infected with influenza viruses, and methods of inhibiting influenza virus replication in an individual infected therewith, comprising administering to the individual an effective anti-viral dose of an anti-M2e antibody of the invention or a pharmaceutical formulation thereof.

DETAILED DESCRIPTION OF THE INVENTION

Figure 1:
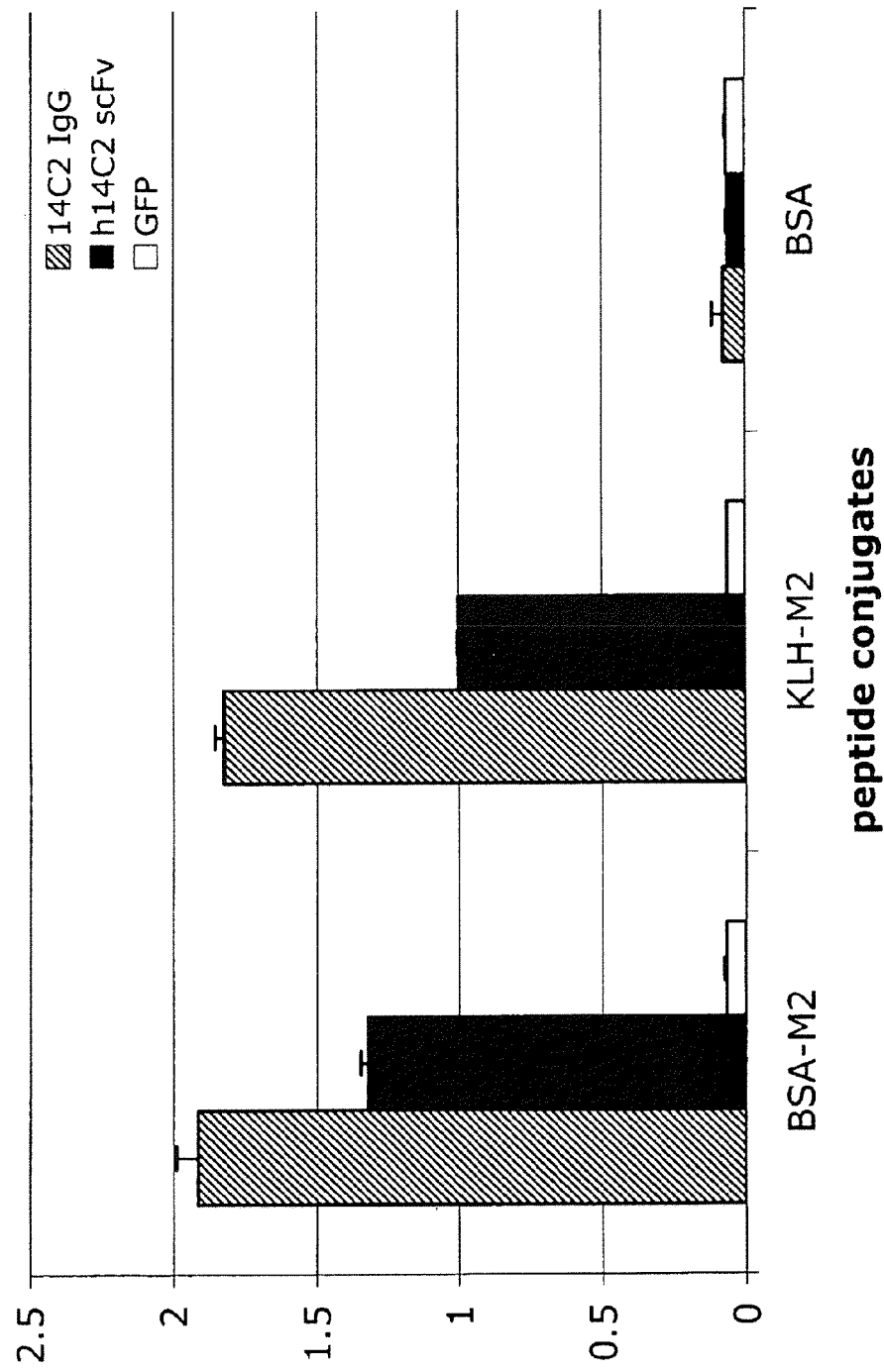
FIG. 1. Recognition of the conM2 peptide by h14C2 scFv and the parental mAb, 14C2. See Example 1, infra.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001). As appropriate, procedures involving the use of commercially available kits and reagents are generally carried out in accordance with manufacturer defined protocols and/or parameters unless otherwise noted.

The terms "antibody" and "immunoglobulin" are used interchangeably in the broadest sense and includes monoclonal antibodies, polyclonal antibodies, multivalent antibodies, and multi specific antibodies (e.g., bispecific antibodies so long as they exhibit the desired biological activity), regardless of how they are produced (i.e., using immunization, recombinant, synthetic methodologies). As used herein, the term antibody also includes derivatives, such as scFv (single chain antibody) and minibodies (bivalent, homodimeric scFv derivative).

The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light" chain, domain, region and component are used interchangeably, are abbreviated by "VL" or "$V_L$" and refer to the light chain of an antibody or antibody fragment. Similarly, terms "variable heavy" chain, domain, region and component are used interchangeably, are abbreviated by "VH" or "$V_H$" and refer to the heavy chain of an antibody or antibody fragment.

The terms "anti-M2e antibody" and "M2e antibody" are used interchangeably and refer to antibodies that are specific for and bind specifically to the ectodomain of the influenza M2 ion channel protein.

As used herein, the terms "specific", "specifically reactive", "specific binding", "specifically binds" and "binds specifically" when used in connection with the antibodies and antibody fragments of the invention refer to the selective binding of M2e antibodies to the influenza M2 protein, more specifically to the ectodomain of the M2 protein. Specificity is generally determined using standard immunological assays, including without limitation ELISA, immunoblot, Western Blot, immunohistochemical and immunoprecipitation assays, under conditions typically employed for conducting such assays. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity).

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG-1, IgG-2, IgA-1, IgA-2; and etc. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not as antibody fragments as defined below. The terms particularly refer to an antibody with heavy chains that contain the Fc region. A full length antibody can be a native sequence antibody or an antibody variant.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment which consists of a VH domain; (vii) isolated CDR regions; (viii) F(ab')$_2$ fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain (VH) connected to a light chain variable domain (VL) in the same polypeptide chain; (xi) "linear antibodies" comprising a pair of tandem Fd, segments (VH-CH1-VH-CH1) which, together with complementary light chain polypeptides, form a pair of antigen binding regions.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain.

As used herein, the term "single-chain Fv" or "scFv" or "single chain" antibody refers to antibody fragments comprising the VH and VL domains of antibody, wherein these domains are present in a single polypeptide chain connected by a polypeptide linker. Generally, the Fv polypeptide further comprises a polypeptide linker between the VH and VL domains which enables the sFv to form the desired structure for antigen binding. For a review of sFv, see Pluckthun, THE PHARMACOLOGY OF MONOCLONAL ANTIBODIES, vol. 113, Rosenburg and Moore eds. Springer-Verlag, New York, pp. 269-315 (1994).

The terms "anti-M2e antibody fragment" and "M2e antibody fragment" are used interchangeably and refer to antibody fragments that specifically bind to the ectodomain of the influenza M2 protein. The terms "anti-M2e scFv", anti-M2e single chain antibody", "M2e scFv", and "M2e single chain antibody" are used interchangeably and refer to single chain antibodies that specifically bind to the ectodomain of the influenza M2 protein.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. The monoclonal antibodies of the invention may be generated by recombinant DNA methods, and are sometimes referred to as "recombinant antibodies" or "recombinant monoclonal antibodies" herein.

Recombinant antibody fragments may be isolated from phage antibody libraries using techniques well known in the art. See, for example, Clackson et al., 1991, Nature 352: 624-628; Marks et al., 1991, J. Mol. Biol. 222: 581-597. Recombinant antibody fragments may be derived from large phage antibody libraries generated by recombination in bacteria (Sblattero and Bradbury, 2000, Nature Biotechnology 18:75-80; and as described herein). Polynucleotides encoding the VH and VL components of antibody fragments (i.e., scFv) may be used to generate recombinant full length immunoglobulins using methods known in the art (see, for example, Persic et al., 1997, Gene 187: 9-18).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al., Nature 305:537-39 (1983). Alternatively, bispecific antibodies can be prepared using chemical linkage. See, e.g., Brennan, et al., Science 229:81 (1985). Bispecific antibodies include bispecific antibody fragments. See, e.g., Hollinger, et al., Proc. Natl. Acad. Sci. U.S.A. 90:6444-48 (1993), Gruber, et al., J. Immunol. 152:5368 (1994).

An "affinity matured" antibody is one with one or more modifications (mutations) in one or more CDRs thereof which result in an improvement in the affinity of the antibody for antigen, compared to the unmodified parent antibody. Preferred affinity matured antibodies will have nanomolar or even picomolar affinities for the target antigen. Affinity matured antibodies are produced by various procedures known in the art, including by variable domain shuffling (see, e.g., Marks et al. 1992, Bio/Technology 10:779-783), random mutagenesis of CDR and/or framework residues (see, e.g., Barbas et al., 1994, Proc Nat. Acad. Sci, USA 91:3809-3813; Schier et al., 1995, Gene 169:147-155; Yelton et al., 1995, J. Immunol. 155:1994-2004; Jackson et al., 1995, J. Immunol. 154(7):3310-9; and, Hawkins et al, 1992, J. Mol. Biol. 226: 889-896).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides or ribonucleotides and polymers thereof ("polynucleotides") in either single- or double-stranded form. Unless specifically limited, the term "polynucleotide" encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19: 5081; Ohtsuka et al., 1985 J. Biol. Chem. 260: 2605-2608; and Cassol et al., 1992; Rossolini et al., 1994, Mol. Cell. Probes 8: 91-98). The term nucleic acid is used interchangeably with gene, cDNA, and mRNA encoded by a gene.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "vector" refers to a nucleic acid molecule capable of transporting another nucleic acid to which it has been linked. For example, one type of vector is a plasmid, a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Certain vectors are capable of directing the expression of genes to which they are operatively linked. Such vectors are referred to herein as "recombinant expression vectors" or "expression vectors".

The term "host cell" (or "recombinant host cell"), as used herein, refers to a cell that has been genetically altered, or is capable of being genetically altered by introduction of an exogenous polynucleotide, such as a recombinant plasmid or vector, and includes not only the particular subject cell but also the progeny thereof. Because certain modifications may occur in succeeding generations due to either mutation or environmental influences, such progeny may not, in fact, be identical to the parent cell, but are still included within the scope of the term "host cell" as used herein.

The term "link" as used herein refers to a physical linkage as well as linkage that occurs by virtue of co-existence within a biological particle, e.g., phage, bacteria, yeast or other eukaryotic cell.

"Physical linkage" refers to any method known in the art for functionally connecting two molecules (which are termed "physically linked"), including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

"Fused" refers to linkage by covalent bonding.

As used herein, "linker" or "spacer" refers to a molecule or group of molecules that connects two molecules, such as VH and VL genes or polypeptides (i.e., in a scFv), and serves to place the two molecules in a preferred configuration.

The term "isolated" refers to material which is substantially or essentially free from components which normally accompany the material as it is found in its native or natural state. However, the term "isolated" is not intended refer to the components present in an electrophoretic gel or other separation medium. An isolated component is free from such separation media and in a form ready for use in another application or already in use in the new application/milieu. An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The terms "label" and "detectable label" refer to a detectable compound or composition which is conjugated directly or indirectly to the antibody so as to generate a "labeled" or "detectably labeled" antibody. The label may be detectable by itself (e.g. radioisotope labels or fluorescent labels) or, in the case of an enzymatic label, may catalyze chemical alteration of a substrate compound or composition which is detectable. A great number of such labels are known in the art, including without limitation protein tags, radioisotopes, metal chelators, enzymes, fluorescent compounds (dyes, proteins, chemicals), bioluminescent compounds, and chemiluminescent compounds.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a fluorescent protein from one source and a nucleic acid encoding a peptide sequence from another source. Similarly, a heterologous protein indicates that the protein comprises two or more subsequences that are not found in the same relationship to each other in nature (e.g., a fusion protein).

In one aspect, the invention provides a humanized anti-M2e monoclonal antibody with anti-viral activity against influenza viruses. The anti-M2e antibody of the invention is specific for the ectodomain of the influenza M2 ion channel protein, and comprises a light chain variable region having the amino acid sequence of SEQ ID NO: 1, and a heavy chain variable region having the amino acid sequence of SEQ ID NO: 2. In preferred embodiments, the anti-M2e antibody is isolated, purified or semi-purified such that they retain specificity in the desired application. The anti-M2e antibodies of the invention may be of the immunoglobulin classes IgA, IgD, IgE, IgG and IgM and subclasses thereof, although for therapeutic applications, monoclonal IgG formulations may be preferred. A related aspect of the invention relates to anti-M2e antibody fragments. The anti-M2e antibody fragments of the invention are specific for a the ectodomain of the influenza M2 protein, and may be generated from intact antibodies or through the use of recombinant technology, as is well known in the art.

Anti-M2e antibodies (scFv and minibody) were generated as described in Example 1, infra. Briefly, using a approach which combined various antibody humanization strategies, a humanized version of the murine monoclonal antibody 14C2 (an anti-M2e antibody) was generated as a single chain Fv (scFv). Once recognition of the M2 peptide was established for the humanized h14C2 scFv it was converted into the minibody format (Di Niro, et al., 2007), in which the scFv is fused directly to either human or murine CH2-CH3 domains. Minibodies are similar to full length antibodies in their activity, but have the advantage that only one gene is required, making cloning and expression considerably easier. The minibody derivatives had equivalent specificity to the original mAb and recognized native M2 proteins as shown by a variety of assays including flow cytometry, western blot and ELISA (see Example 1). They also show in vitro activity against influenza, by reducing the size and number of plaques. However, the in vitro activity of the humanized minibody was dependent upon high concentrations of minibody. It has been previously shown that the anti-viral activity of the 14C2 mAb is dependent upon the bivalent structure of the Ab, since Fab fragments do not restrict virus replication (Hughey, et al., 1995). While the minibody scFv binding sites are dimerized in the minibody construct, the lack of the CH1 domain reduces the distance that the two scFvs can span, and this may account for the lower activity, that can be overcome by higher concentrations.

The anti-M2e antibodies and antibody fragments of the invention may be detectably labeled as is generally known. The label may be detectable by itself (e.g. radioisotope labels or fluorescent labels) or, in the case of an enzymatic label, may catalyze chemical alteration of a substrate compound or composition which is detectable. A great number of such labels are known in the art, including without limitation protein tags, radioisotopes, metal chelators, enzymes, fluorescent compounds (dyes, proteins, chemicals), bioluminescent compounds, and chemiluminescent compounds.

Another aspect of the invention relates to polynucleotides encoding the M2e antibodies and antibody fragments of the invention, as well as vectors and expression vectors comprising such polynucleotides. The polynucleotides and expression vectors of the invention are useful for the production of the antibodies and antibody fragment of the invention.

anti-M2e antibody- and antibody fragment-encoding polynucleotides may be inserted into vectors capable of directing the expression of the desired antibody product in both prokaryotic and eukaryotic host cells. A number of antibody expression vectors have been described, and methods for generating antibodies and antibody fragments are well known in the art. See, for example, Delves, ANTIBODY PRODUCTION: ESSENTIAL TECHNIQUES (Wiley, 1997); Shephard, et al., MONOCLONAL ANTIBODIES (Oxford University Press, 2000); Coding, MONOCLONAL ANTIBODIES: PRINCIPLES AND PRACTICE (Academic Press, 1993); CURRENT PROTOCOLS IN IMMUNOLOGY (John Wiley & Sons, most recent edition).

In one embodiment, phage display systems are used to select M2e single chain antibodies. Once isolated, polynucleotides encoding specific M2e scFvs may be cloned into expression vectors designed to express full length immunoglobulins as well as fragments thereof having the same specificity. Briefly, the $V_H$ and $V_L$ genes of the single chain antibody are cloned into an immunoglobulin scaffold (i.e., IgG) vector, expressed, and dimerized in order to 'convert' the single chain into a full antibody. The immunoglobulin scaffold may be selected from any of the five major classes of immunoglobulins (IgA, IgD, IgE, IgG and IgM), and subclasses thereof (i.e., IgG-1). Recombinant M2e antibodies which are to be used therapeutically in an animal in vivo should be based on an immunoglobulin scaffold that matches the immunoglobulins of the animal. Example 1 describes the generation and characterization of a humanized anti-M2e monoclonal antibody suitable for human therapeutic applications.

Methods for the conversion of scFvs into intact immunoglobulin molecules are well known, and include without limitation, the methods and expression vectors described in Persic et al., 1997, *An integrated vector system for the eukaryotic expression of antibodies or their fragments after selection from phage display libraries*. Gene 187: 9-18). See also, WO 94/11523, WO 97/9351, EP 0481790.

The M2e antibodies of the invention may be modified to increase binding affinity, improve stability, and the like, using standard techniques. For example, substitutions, deletions and insertions of amino acids in the antibody polypeptides may be introduced (see, infra).

Recombinant anti-M2e antibodies of the invention may be generated using both prokaryotic and eukaryotic expression systems. It is not necessary that the recombinant antibodies of the invention be glycosylated or expressed in eukaryotic cells, although expression in mammalian cells is generally preferred. Various prokaryotic expression host cells may therefore be useful in the generation of such recombinant M2e antibodies and fragments. Bacterial expression systems are preferred, and a wide variety of appropriate expression vectors and methods are known. *E. coli* host cells are preferred.

In bacterial expression systems, the expressed light and heavy chain polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, the antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis, trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J. Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210. Sufficient disulfide bonds are particularly important for the formation and folding of full length, bivalent antibodies having two heavy chains and two light chains.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease 1, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Nara et al., Microbial Drug Resistance, 2:63-72 (1996).

In a preferred embodiment, *E. coli* strains deficient for proteolytic enzymes and transformed with plasmids overexpressing one or more chaperone proteins are used as host cells in the expression system of the invention. Some of these strains are further described in the Examples section below.

Heavy and light chains may be expressed from a single construct or using multiple constructs (expression vectors). For example, United States patent application of Simmons et al., No. 20050170464, describes a process for producing an immunoglobulin in a prokaryotic host cell, using a "separate cistron" expression vector containing a first promoter-cistron pair for expression of an immunoglobulin light chain and a second promoter-cistron pair for expression of an immunoglobulin heavy chain, whereby expression of the light chain and heavy chain are independently regulated by separate promoters. Each cistron within the expression cassette polynucleotide comprises a translation initiation region (TIR) operably linked to the nucleic acid sequence coding for the light chain or heavy chain of the full length antibody. According to this method, the TIR sequences within the expression vector of the invention are manipulated so to provide different translational strength combinations for light and heavy chains.

When using recombinant techniques, the antibody can be produced intracellularly or in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology, 10: 163-167 (1992) describes a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an AMICON™ or MILLIPORE PELLICON™ ultrafiltration unit. A protease inhibitor such as phenylmethylsulfonylfluoride fluoride (PMSF) may be included in any of the foregoing steps to inhibit proteolysis, and antibiotics may be included to prevent the growth of adventitious contaminants.

In another aspect of the invention, the variable heavy and light chains of recombinant M2e antibody fragments may be multimerized (i.e., scFvs may be multimerized) to increase binding affinity, by for example, in vitro biotinylation and avidin capture to isolate tetramers. Various strategies have been developed for preparing scFv as a multimeric derivative. This is intended to lead, in particular, to recombinant antibodies with increased binding avidity. In order to achieve multimerization of the scFv, scFv are prepared as fusion proteins with multimerization domains. The multimerization domains may be, e.g. the CH3 region of an IgG or coiled coil structure (helix structures) such as Leucine-zipper domains. However, there are also strategies in which the interaction between the VH/VL regions of the scFv are used for the multimerization (e.g. di-, tri- and pentabodies). Diabodies are a bivalent homodimeric scFv derivative (Hu et al., 1996, PNAS 16: 5879-5883). The shortening of the linker in an scFv molecule to 5-10 amino acids leads to the formation of homodimers in which an inter-chain VH/NL-superimposition takes place. Diabodies may additionally be stabilized by the incorporation of disulphide bridges. Examples of diabody-antibody proteins may be found in Perisic et al., 1994, Structure 2: 1217-1226. By minibody the skilled person means a bivalent, homodimeric scFv derivative. It consists of a fusion protein which contains the CH3 region of an immunoglobulin, preferably IgG, most preferably IgG1 as the dimerization region which is connected to the scFv via a Hinge region (e.g. also from IgG1) and a Linker region. The disulphide bridges in the Hinge region are mostly formed in higher cells and not in prokaryotes. Examples of minibody-antibody proteins may be found in Hu et al., 1996, Cancer Res. 56: 3055-61. A triabody is a trivalent homotrimeric scFv derivative wherein VH-VL are fused directly without a linker sequence leading to the formation of trimers (see, for example, Kortt et al. 1997 Protein Engineering 10: 423-433).

Suitable host cells for cloning or expressing the polynucleotides in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g. *B. licheniformis* 41 P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for M2e antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183, 070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated anti-M2e antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g. the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells/-DHFR (CHO, Urlaub et al., Proc. Natl. Acad. Sci. USA, 77:4216 (1980), including DG44 (Urlaub et al., Som. Cell and Mol. Gen., 12: 555-566 (1986)) and DP12 cell lines); mouse sertoli cells (TM4, Mather, Biol. Reprod., 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci., 383:44-68 (1982)); MRC 5 cells; FS4 cells; and a human hepatoma line (Hep G2).

Host cells are transformed or transfected with the above-described expression or cloning vectors (or these vectors are otherwise introduced, for example by chemical transfection methods) for M2e antibody production and cultured in conventional nutrient media modified as appropriate for inducing promoters, selecting transformants, or amplifying the genes encoding the desired sequences.

The host cells used to produce the M2e antibodies of the invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described, for example, in Ham et al., Meth. Enz. 58:44 (1979); Barnes et al., Anal. Biochem., 102:255 (1980); U.S. Pat. Nos. 4,767,704; 4,657,866; 4,927,762; 4,560,655; or 5,122,469; WO 1990/03430; WO 1987/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In a preferred embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41 kD cell wall protein from *Staphylococcus aureus* which binds with a high affinity to the Fc region of antibodies. Lindmark et al (1983) J. Immunol. Meth. 62:1-13. The solid phase to which Protein A is immobilized is preferably a column comprising a glass or silica surface, more preferably a controlled pore glass column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the full length antibody to Protein A. The solid phase is then washed to remove contaminants non-specifically bound to the solid phase. Finally the full length antibody is recovered from the solid phase by elution.

Another aspect of the invention relates to antibody variants. Amino acid sequence modification(s) of the M2e antibodies and fragments of the invention are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed full length antibodies are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but framework region alterations are also contemplated.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the full length antibody of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

Antibody derivatives are also included in the invention. In this regard, the antibodies and antibody variants of the present invention can be further modified to contain additional non-proteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and or type of polymers used for derivatization can be determined based on considerations including, but not limited to, the particular properties or functions of the antibody to be improved, whether the antibody derivative will be used in a therapy under defined conditions.

The anti-M2e antibodies of the invention (i.e., the monoclonal M2e antibody) may be used as a passive vaccine and/or as therapeutic to treat influenza infection. Typically, for the treatment of human subjects, the antibody is formulated into a pharmaceutical composition comprising a carrier suitable for the desired delivery method ("pharmaceutically acceptable carrier"). Suitable carriers include any material which when combined with the anti-M2e antibody retains the antiviral function of the antibody and is non-reactive with the subject's immune systems. Examples include, but are not limited to, any of a number of standard pharmaceutical carriers such as sterile phosphate buffered saline solutions, bacteriostatic water, and the like.

Anti-M2e antibody formulations may be administered via any route capable of delivering the antibodies to cells in which the influenza virus replicates as well to assembling influenza virions and intact virus particles. Potentially effective routes of administration include, but are not limited to, intravenous, intraperitoneal, intramuscular, intradermal, and the like. The preferred route of administration is by intravenous injection. A preferred formulation for intravenous injection comprises the anti-M2e mAb in a solution of preserved bacteriostatic water, sterile unpreserved water, and/or diluted in polyvinylchloride or polyethylene bags containing 0.9% sterile Sodium Chloride for Injection, USP. The anti-M2e mAb preparation may be lyophilized and stored as a sterile powder, preferably under vacuum, and then reconstituted in bacteriostatic water containing, for example, benzyl alcohol preservative, or in sterile water prior to injection.

The M2e antibodies and antibody fragments of the invention will also be useful in a wide variety of immunological protein assays and isolation procedures, including without limitation, ELISAs, Western Blots and other immunoblot techniques, immunohistochemical assays, various affinity purification methods, and the like. Accordingly, the invention provides various immunological assays useful for the detection of the ectodomain of the influenza M2 protein.

EXAMPLES

Example 1

Humanization of M2e Monoclonal Antibody

Materials and Methods

Viruses, Cell Lines, and Monoclonal Antibodies

The influenza virus used in these studies was A/Udorn/307/72 (A/Udorn, kindly provided by Dr. Suzanne Epstein, FDA/CBER, Bethesda, Md., USA). A/Udorn was cultured in the allantoic cavity of 9 day-old embryonated chicken eggs for 3 days at 35° C. Allantoic fluid was collected, cleared by centrifugation, aliquoted, and stored at −80° C. Virus titers were confirmed by $TCID_{50}$, plaque, and/or hemagglutination assays as described. Madin-Darby canine kidney (MDCK) cells (ATCC) were cultured in DMEM containing 5-10% FBS. FreeStyle™ 293-F cells (293-F; Invitrogen, Carlsbad, Calif., USA) were cultured according to the manufacturer's instructions. The hybridoma for the 14C2-S1-4 mAb (IgG2a; gift of Dr. Walter Gerhard, The Wistar Institute, Philadelphia, Pa., USA) was cultured in DMEM+10% FBS. The hybridoma for the purified mouse control mAb, anti-influenza NP (IgG2a, gift of Dr. Jon Yewdwll, NIAID, Bethesda, Md., USA) was cultured in DMEM+10% FBS.

scFv and Minibody Cloning

The h14C2 VH and VL genes were ordered from Blue Heron Biotechnology. They were cloned individually into phage display vector pDAN5 (Sblattero and Bradbury, 2000) using BssHII and BspEI for VL and KpnI and NheI for VH. The characteristics, and the cloning procedures, of the mouse and the human version of the constructs encoding for miniantibodies are reported in detail in (Di Niro et al., 2008), specifically, the cloning of the h14C2 scFv, as well as of the control D1.3 (Mariuzza et al., 1983) was performed by excising the scFv genes from the pDAN5 phage display vector using BssHII and NheI and cloning directly into the minibody constructs using the same enzymes, and so replacing the resident 2.8 scFv gene.

scFv Expression

The pDAN5 plasmids containing scFvs (h14C2 or D1.3, the control scFv) were transformed into DH5αF', grown on 2×TY agar plates (containing 3% glucose and carbenicillin 50 µg/ml). The following day a small streak of bacteria was added to 10 ml of carbenicillin/glucose 2×TY media and grown to 0.5 $OD_{600}$. The bacteria were centrifuged and re-suspended in 10 ml of carbenicillin/IPTG (250 mM) 2×TY media and protein production was allowed to proceed at 30° C. overnight. The following day, bacteria were centrifuged and the culture supernatant used in ELISA.

Peptide Synthesis

The M2con peptide was synthesized on a CEM microwave synthesizer using standard 0.1 mmol Fmoc chemistry. All reagents were Biochem or HPLC grade obtained through Sigma Aldrich, Novabiochem or Fisher Scientific, respectively. The peptides were deprotected with TFA/Water/TIS (95:2.5:2.5) and DTT added (2 mg/mL). Crude peptide purities were in excess of 70% and the peptides were purified using a linear gradient from 92:8 to 60:40 Water/ACN with 0.1% TFA. Analyses of the purified peptides were obtained on a Thermo Electron LCQ Deca in ESI+mode with $M^{2+}$ of the peptides seen as dominant signal. The peptide was obtained in over 50% of theoretical yield in >98% chemical purities.

ELISA Testing of scFv on M2 Peptides

Unlabeled purified M2 peptide was conjugated to BSA and KLH using Imject maleimide activated supercarrier immune modulator (BSA) and mcKLH (Pierce Inc.) kits according to the manufacturer's instructions. The success of conjugation was evaluated by 14C2 IgG based ELISA. Antigens were added to Nunc. Maxisorp 96 well plate at 1 µg/100 µl concentration and incubated at 4° C. overnight. Excess protein was washed with PBSLT (1×PBS with 0.01% tween) and 200 µl of wonder block (0.3% BSA, 0.3% milk, 0.3% fish gelatin) and incubated for 1 hour at RT. After washing with PBSLT, 70 µl of scFv culture supernatant and 30 ml blocking agent was added per well and incubated for 1 hour. Unbound reagents were washed using PBST (1×PBS with 0.1% tween) and PBSLT. The bound scFv was detected using anti-SV5 antibody (1 mg/ml) followed by anti-mouse HRP (Dako Inc. 0.5 mg/ml). The HRP activity was detected using TMB (Sigma, Inc.) and quenched with 1M $H_2SO_4$. ELISA values are given as absorbance at 450 nm. The mouse 14C2 IgG was purchased from Affinity BioReagents Inc. and used at 1 mg/ml concentration. Its binding was also detected as described.

Expression of scFv in 293 Cells

The various minibody constructs were expressed using the FreeStyle™ 293 Expression System (Invitrogen), following the manufacturer's instructions. In brief, 293-F cells were cultured in suspension in FreeStyle™ 293 Expression Medium, transfected with 300 µg of plasmid per 250 ml of cells and cultured for 72 hours. Culture supernatants were collected, filtered and assayed for minibody expression by M2-specific assay, V5 epitope or Fc in western blot and ELISA assays. In some cases, scFvs were purified using HiTrap™ protein G columns (GE Healthcare) or ProPur Protein A spin columns (Nunc, Rochester, N.Y., USA) following standard procedures. To assess concentrations of minibodies in culture supernatants, purified minibodies and culture supernatants were titered and assayed by western blot. Proteins were detected by V5 tag and concentration in supernatants determined as compared to the purified minibodies using densitometry.

Creation of HEK 293 M2 Cell Lines

The M2 cDNA from influenza A/PR/8/34 (PR8-M2, GenBank accession #AF389121.1) was synthesized and cloned into the pJ5 vector (Integrated DNA Technologies, Coralville, Iowa, USA) with HindIII and EcoRV restriction sites at the 5' and 3' end, respectively. PR8-M2 was cloned by restriction digest and ligation into pcDNA5/FRT/TO (Invitrogen). Cloning was confirmed by sequence analysis. To generate the M2 consensus construct (conM2) the pcDNA5/FRT/TO-M2-PR8 plasmid was mutated using QuickChange Site-Directed Mutagenesis Kit (Stratagene, La Jolla, Calif., USA) following the manufacturer's instructions. In brief, nucleotides 61-63 of the cDNA were altered from GGT to GAT, changing Glycine 21 to Aspartic Acid, converting the PR8M2e sequence to the consensus M2e sequence. The mutation was confirmed by sequence analysis. The new construct, pcDNA5/FRT/TO-conM2 has the consensus M2e sequence and PR8 transmembrane and cytoplasmic sequences.

The inducible 293-M2 cell lines were generated using the Flp-In™ T-REx™ 293 Cell Line system (Invitrogen) following the manufacturer's instructions. This system enables insertion of a cDNA into a unique insertion site in the genome using site-specific DNA recombination. Gene expression is regulated by a Tet repressor and is induced by the addition of tetracycline. 293-M2 cells were cultured in DMEM containing 10% FBS containing blasticidin and hygromycin. The M2 expression was induced by adding tetracycline to the media (1 µg/ml final). Cells were incubated for 72 hours, fixed, and M2 expression measured by flow cytometry using the M2-specific mAb, 14C2-S1-4. M2 positive clones of 293-PR8M2 and 293-conM2 were selected and used throughout the studies.

Cell ELISA

The cell-based ELISA for M2-specific antibody binding was done as previously described (Feng, et al., 2006) with modifications. In brief, 239 control, 293-PR8M2, or 293-conM2 cells were plated in 96-well tissue culture plates in DMEM containing 10% FBS and tetracycline (1 µg/ml final; to induce M2 expression), and incubated at 37° C., 5% $CO_2$. In some experiments control wells included 293-PR8M2 or 293-conM2 without tetracycline induction. Seventy-two hours later, plates were gently washed with PBS, fixed with 4% formaldehyde, washed, and then blocked with PBS containing 5% non-fat dry milk and 0.5% BSA. Antibodies or minibodies were serially diluted in PBS containing 1% BSA and incubated with the cells for 2 hours at 37° C. Plates were washed and incubated with secondary antibody (goat anti-mouse IgG (H+L) or goat anti-human IgG (H+L) phosphatase labeled; Kirkegaard & Perry Laboratories, Inc, Gaithersburg, Md., USA). Plates were developed with pNPP Phosphatase Substrate (Kirkegaard & Perry Laboratories) following the manufacturer's instructions. Absorbance was measured at 405 nm on a 96-well plate reader (BioTek Instruments, Inc., Winooski, Vt., USA).

Flow Cytometry

Control 293, 293-PR8M2, and 293-conM2 cells were cultured in DMEM containing 10% FBS with or without tetracycline (1 µg/ml final) to induce M2 expression. Seventy-two hours later, cells were harvested by washing with PBS (no $Mg^{++}$ or $Ca^{++}$)+2.5 mM EDTA, fixed with 4% formaldehyde, washed, and then blocked with PBS containing, 2% FBS, 0.02% azide, and FcBlock (BDPharmingen). Antibodies or minibodies were diluted in PBS containing 2% FBS+0.02% azide and incubated with the cells for 20 minutes at on ice. Cells were washed and incubated with secondary antibody (goat anti-mouse IgG-Alexa 488 or goat anti-human IgG-Alexa 488, Invitrogen) in PBS containing 2% FBS+0.02% azide for 30 minutes on ice. Fluorescence was measured on a LSR II flow cytometer (BD Biosciences, San Jose, Calif., USA).

Western Blotting

Control 293, 293-PR8M2, and 293-conM2 cells were cultured, induced, and harvested as in the flow cytometry protocol. Cells were then either fixed with 4% formaldehyde or left untreated. All samples were then lysed using PBS containing 0.5% Triton X-100. The lysates were briefly sonicated and separated in non-reducing 12.5% Tris-HCl, SDS-PAGE gels following standard protocols. The separated proteins were transferred to PVDF membranes (Millipore) and blocked using TBS-0.05% Tween 20 containing 5% non-fat dry milk. Blots were incubated with antibodies or minibodies (diluted in TBS-0.05% Tween 20+2% non-fat dry milk, washed and then incubated with detection antibody (goat anti-mouse IgG (H+L) or goat anti-human IgG (H+L) phosphatase labeled; Kirkegaard & Perry Laboratories, Inc). Blots were developed using ECF reagent (GE Healthcare, Piscataway, N.J., UDA) and imaged using a Typhoon Imager (GE Healthcare).

In Vitro Plaque Inhibition Assay

MDCK cells were plated into 12 well plates and allowed to grow to near-confluence. Approximately 30 pfu of A/Udorn virus was diluted into MEM containing 1 µg/ml TPCK-treated trypsin (Worthington Biochemical, Lakewood, N.J., USA) and antibody or minibody as indicated. Virus with minibody were incubated for 30 minutes at 4° C. The plates were washed with MEM to remove serum-containing medium and the virus was added to each well in 0.1 ml. Cells were infected for 2 hours at 37° C. and then overlaid with MEM+1.2% Avicel (Matrosovich et al., 2006), 1 µg/ml TPCK-treated trypsin, and antibody or minibody at the indicated concentrations. Plates were incubates at 37° C. for 2 days, the overlay gently washed off using PBS, fixed with ice-cold methanol/acetone (40%:60%), air-dried, and the plaques visualized by crystal violet counter-stain. Plates were imaged on a Typhoon Imager and plaques counted manually.

Results

M2e Conservation

The sequences of M2e proteins from all influenza A infecting humans were downloaded from the Los Alamos influenza database (Macken et al., 2001). This was pared down from 1476 to 1353 sequences after all partial sequences were removed. Of these 937 (69.2%) are represented by the proposed consensus vaccine sequence (MSLLTEVETP IRNEWGCRCN DSSD; SEQ ID NO: 5) (Neirynck, et al., 1999), and a further 294 (21.7%) differed by only one amino acid, indicating that 90.9% of the N terminal portion of M2e of all sequenced influenza A virus infecting humans are identical to the proposed vaccine strain, or differ from it by only a single amino acid. Of those sequences that differ by more than one amino acid, 78 (5.8%) are represented in the database by less than ten independent isolates. All the H5N1 M2e sequences from viruses that have infected humans differ from the vaccine strain by at least 3 amino acids, with two changes (I11T and N20S) being found in all and one change (G16E) found in most. These changes, however, are not restricted to H5N1: 55 (4.1%) of the non H5N1 strains also show the I11T change, and 34 (2.5%) the N20S change. Table 1 shows a comparison of the different M2e sequences, including the two most common H5N1 sequences.

Antibody Humanization

The VH and VK sequences of 14C2 (Zhang, et al., 2006) were compared to the human VH and VK gene families using IgBLAST (NCBI). As the first seven amino acids of 14C2 were not reported, and a number of other antibodies with the same specificity use the same VH gene, the first seven amino acids of those sequences were used (in italics in Table 2). The closest human V genes were VH1-2 and B3 (VK3). Table 2 shows the homology between the 14C2 sequences and the closest human sequences. These human sequences were used as templates for humanization by assigning a risk score to each amino acid on the basis of an analysis of 6 papers that examined the effects of changing framework residues that might have an effect on affinity (Chothia, et al., 1985, Hwang, et al., 2005, Pedersen, et al., 1994, Roguska, et al., 1994, Studnicka, et al., 1994, Vargas-Madrazo and Paz-Garcia, 2003). At those amino acid positions in which there was a risk of affecting affinity the murine residues were retained, whereas the human residues of VH1-2 and B3 were used at those positions that appeared to have no effect on affinity or where no information on the effect of affinity was available. This approach has been successfully used in the humanization of a botulinum specific antibody without the need for additional mutation (Razai et al., 2005). In total, seven murine amino acids were retained (4 in VH and 3 in VK, underlined in Table 2). The CDRs were transplanted completely, while the J regions used were consensus J sequences. The genes encoding these proteins were synthesized as separate VH and VL genes (Blue Heron Biotechnology), and cloned into pDAN5, our standard phage display vector (Sblattero and Bradbury, 2000).

h14C2 Recognition of M2

In a first test of reactivity the scFv was shown to bind to the conM2 peptide (FIG. 1). For further testing, the scFv was recloned into two minibody constructs, in which the scFv was directly fused to the CH2 of an IgG Fc domain, as previously described (Di Niro et al., 2007). This provides additional stability, dimerization and potential effector functions. Dimerization is particularly important, as it has been shown that monomeric 14C2 Fab does not inhibit viral assembly (Hughey, et al., 1995). The humanized scFv was named h14C2, and the humanized minibody with the h14C2 scFv fused to human CH2 and CH3 constant domains, was named h14C2 human minibody. The murine equivalent, with the h14C2 scFv fused to murine CH2 and CH3 constant regions was named h14C2 murine minibody.

Although recognition of peptide is promising, M2 on the cell surface is present as a tetramer, and it is recognition of cell surface M2, and its subsequent aggregation into coated pits that is responsible for the reduction of virus production observed by some anti-M2 antibodies, such as 14C2 (Hughey, et al., 1995). Furthermore, over 75% of antibodies developed against M2 during virus infection recognize cell expressed M2, but not the synthetic peptide (Feng et al., 2006). For this reason it was important to show that h14C2 recognizes native M2 as expressed on the cell surface. This was addressed using the h14C2 minibodies in three ways: flow cytometry, western blotting and ELISA.

The targets for these experiments were HEK 293 cells transfected with the full length cDNA encoding the M2 gene of A/PR/8/34 or the same construct with a point mutation (G21 D), expressing the consensus M2e. To avoid M2-mediated toxicity, expression of the M2 genes was regulated by a tetracycline-inducible promoter.

Figure 2:
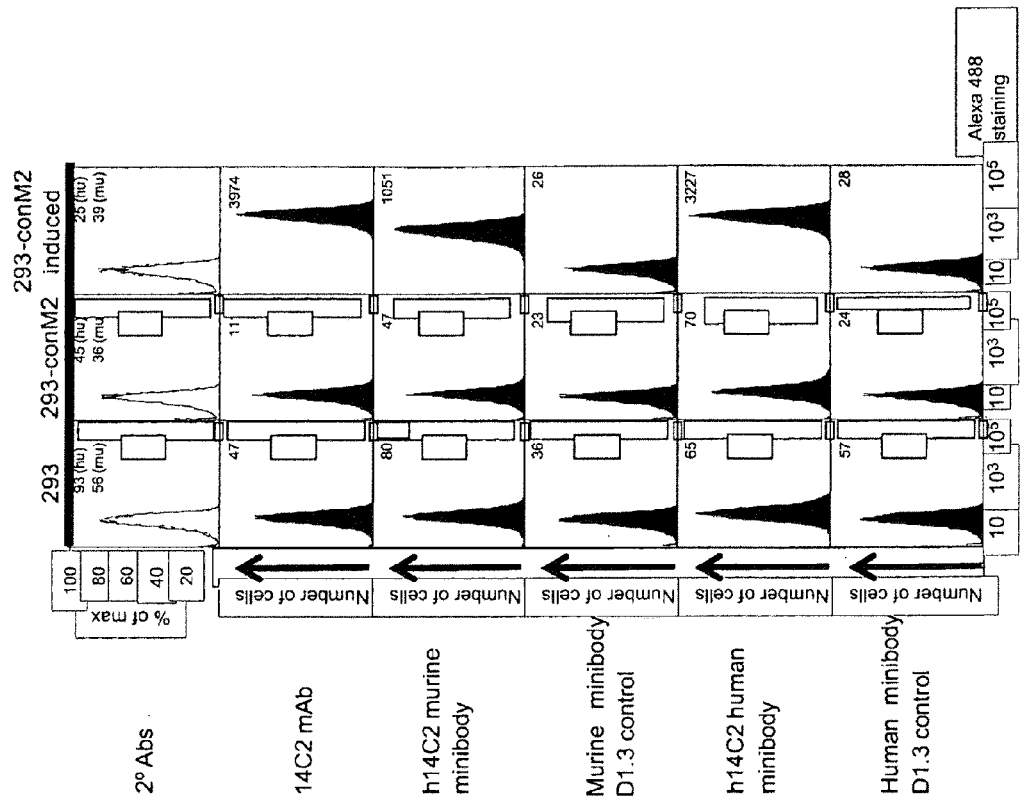
FIG. 2. Recognition of control 293 cells or 293 cells transfected with conM2 gene (induced or not induced) by 14C2, h14C2 murine minibody, and h14C2 human minibody by flow cytometry. Murine secondary antibody controls are represented with dashed lines and human secondary antibody controls are represented with solid lines. Values in the upper right corners of each histogram indicate the mean fluorescent intensity of the peak. See Example 1, infra.
Figure 3:
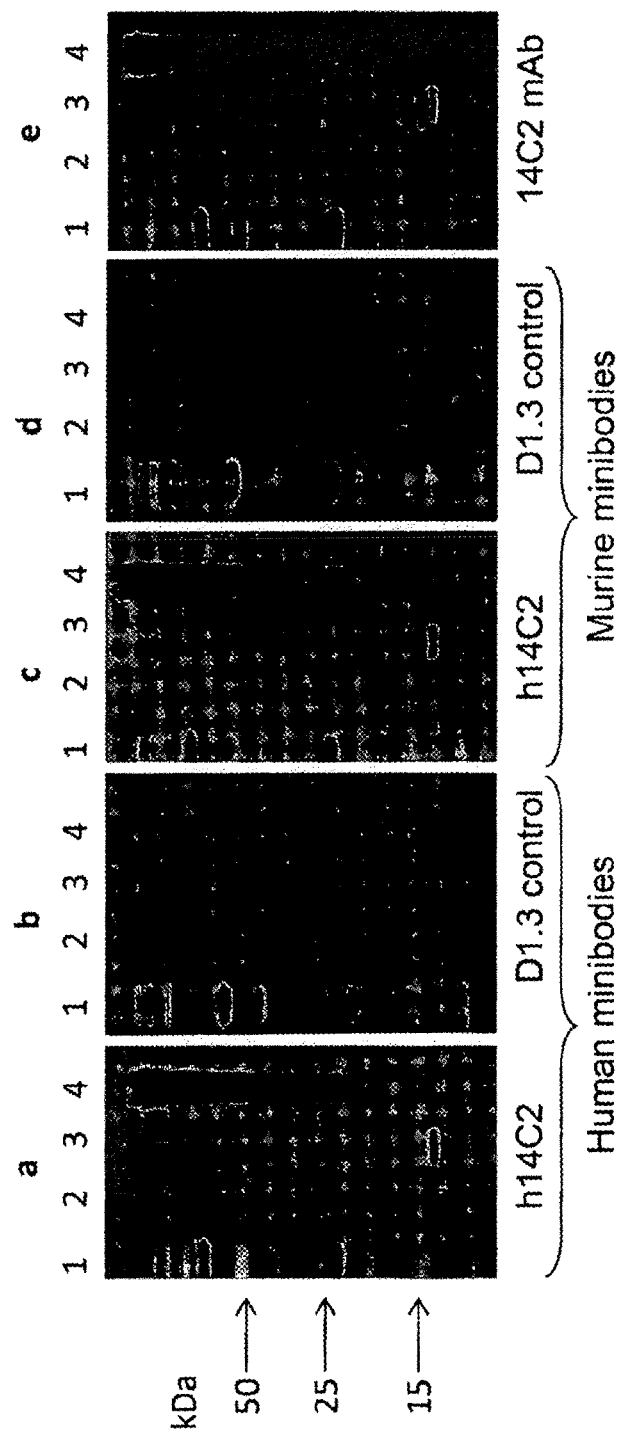
FIG. 3. Western blot recognition of control 293 cells or 293 cells transfected with conM2 gene (induced). Western blot lanes: 1) Marker; 2) 293 cells; 3) 293-conM2; 4) 293-conM2, Fixed. See Example 1, infra.

FIG. 2 shows that cell-expressed M2 proteins were recognized by the original 14C2 murine monoclonal as well as the h14C2 human and murine minibodies in flow cytometry. Signals for the 14C2 mAb and the h14C2 murine minibody are almost comparable as both are recognized by an anti-mouse secondary antibody. However, the murine minibody lacks the CH1 and light chain constant domains, which is likely to reduce the signal somewhat. The h14C2 human minibody is recognized by an anti-human secondary antibody making direct comparison difficult. Notwithstanding these caveats, incubation with equivalent amounts of the mAb and minibodies detected similar levels of the M2 protein on the surface of induced transfectants and showed no reactivity to untransfected or uninduced controls (FIG. 2). Moreover, this confirms that the h14C2 murine minibody is able to recognize M2 within its native context on the cell surface.

During infection, M2 is expressed as a 97 amino acid viroporin present on the cell surface as a tetramer. The M2 proteins form a dimer of homo-dimers (Palese, 2006). Western blots of fixed and non fixed 293-conM2 and control 293 cell lysates were used to test whether the M2-specific minibodies could recognize M2 in the monomeric, dimeric, and/or tetrameric forms. Under standard polyacrylamide gel electrophoresis M2 migrates as a monomer, while fixation prior to reduction maintains M2 in tetrameric, dimeric, and monomeric forms (Feng, et al., 2006). Western blotting with the 14C2 mAb or the human or murine h14C2 minibodies shows (FIG. 3a-e) that all forms (monomer, dimer and tetramer) of M2 are recognized by the humanized minibody, with recognition indistinguishable from that of the parental 14C2 mAb.

Figure 4:
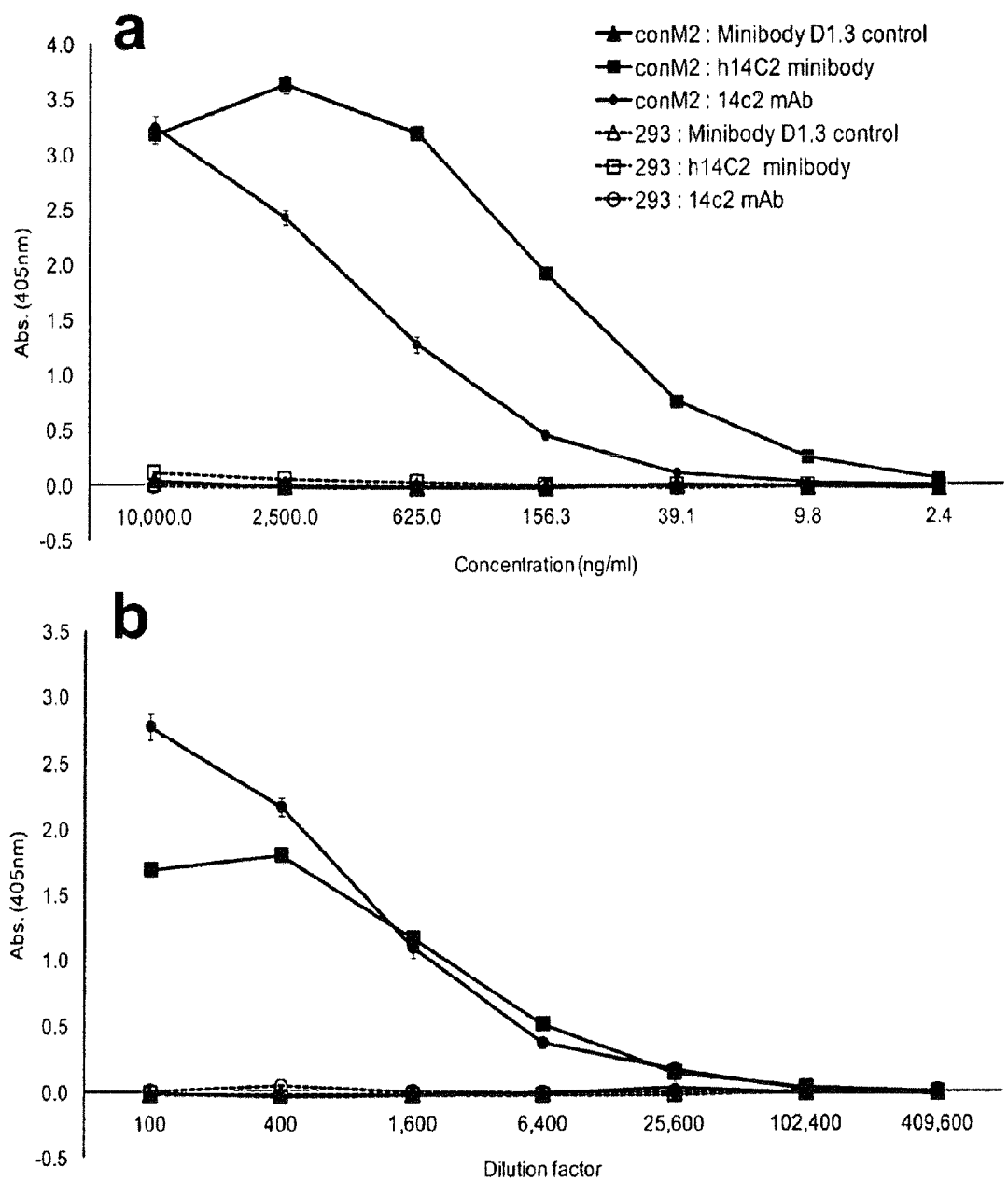
FIG. 4. Recognition of control 293 cells (293) or 293 cells transfected with conM2 gene and induced (conM2) by cell-based ELISA. a) human minibody constructs; b) murine minibody constructs. See Example 1, infra.

Finally, results similar to the flow cytometric analysis were obtained using a cell based ELISA (FIG. 4), in which clear, titratable binding by all M2-specific constructs is shown to the induced and transfected cells, but not the untransfected cells. Fixed cells were incubated with titrated concentrations of 14C2 mAb, h14C2 human minibody, or h14C2 mouse minibody. Purified h14C2 human minibody detected native M2 on the fixed 293-con-M2 cells at least as well as the 14C2 mAb with the h14C2 human minibody titering at approximately 10 ng/ml and 14C2 mAb titering at about 40 ng/ml (FIG. 4a), although absolute comparisons are difficult for the reasons given above. Comparison titrations of supernatants from 14C2 mAb and h14C2 mouse minibody cultures, normalized to equivalent protein concentration by SDS-PAGE densitometry, show that the murine mAb and minibody have similar sensitivities, titering out at a 1:25,600 dilution (FIG. 4b).

m14C2 In Vitro Neutralization Data

The 14C2 mAb has previously been demonstrated to inhibit influenza virus replication in an in vitro plaque-reduction assay (Hughey, et al., 1995, Zebedee and Lamb, 1988). As the h14C2 minibodies recognized native M2 at least as well as the mAb, the ability of the h14C2 murine minibody to inhibit influenza infection was tested in a similar assay. A/Udorn was incubated with 14C2 mAb, h14C2 murine minibody, or mAb control. In each case, the virus was incubated with M2-specific or control constructs at the time of infection and then during the 48 virus culture.

Figure 5:
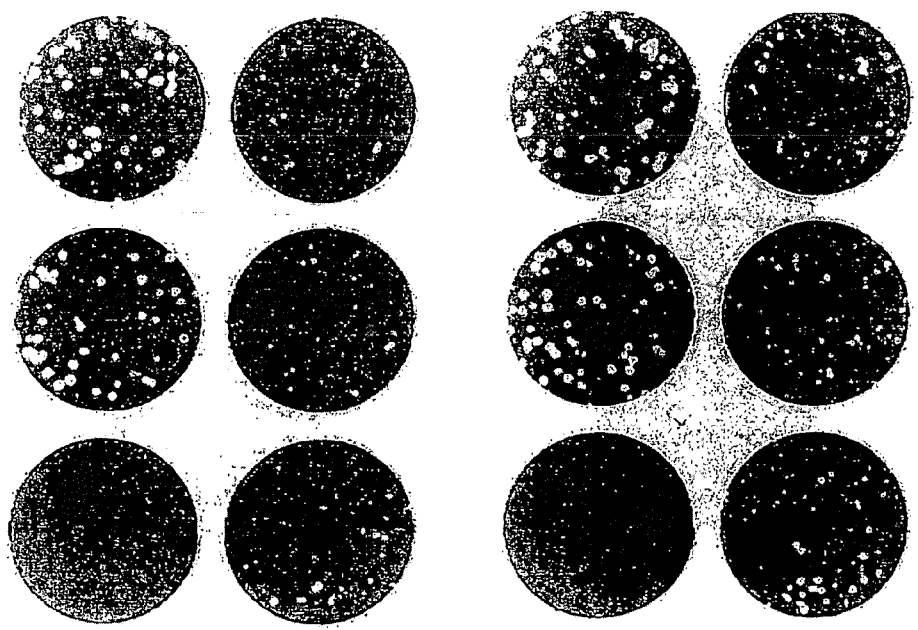
FIG. 5. In vitro plaque inhibition of viral infection: A) A/Udorn virus was cultured into MDCK cells alone (2), in the presence of anti-NP mAb (negative control, 3), or with 25 µg/ml 14C2 mAb (4-6). B) A/Udorn virus was cultured into MDCK cells alone (2), in the presence of anti-NP mAb (negative control, 3), or with 100 µg/ml m14C2 minibody (4-6). Well 1 shows uninfected MDCK cells on each plate. See Example 1, infra.

FIG. 5 shows the reduction of both plaque size and plaque number after incubation with 14C2 mAb alone or the h14C2 mouse minibody. Culture with 100 μg/ml of h14C2 mouse minibody resulted in reductions in plaque size and number, although culture with 25 μg/ml of the 14C2 mAb was sufficient to reduce plaque size and number to a similar extent. Culture with 20 μg/ml of purified 14C2 minibodies was not sufficient to reduce virus replication. Culture with the control mAb did not affect virus replication.

TABLE 1

SEQUENCE CONSERVATION OF M2e

| M2e sequence | | | frequency | Notes |
|---|---|---|---|---|
| MSLLTEVETP | IRNEWGCRCN (SEQ ID NO: 5) | DSSD | 937 | Consensus vaccine conM2 |
| . . . . . . . . . . | . . . . . . . . . . | . . N . | 163 | |
| . . . . . . . . . . | T . . . . . . . . . | . . . . | 45 | |
| . . . . . . . . . . | T . . . . E . . . S | . . . . | 30 | H5N1 |
| . . . . . . . . . . | . . . . . E . . . . | . . . . | 26 | |
| . . . . . . . . . . | . . S . . . . . . . | . . . . | 18 | |
| . . . . . . . . . . | . . . . . Y . . . . | . . . . | 18 | |
| . . . . . . . . . . | . . . . . . . . . . | G . . . | 15 | PR8 |
| . . . . . . . . . . | . . . G . . . . . . | . . . . | 11 | |
| . . . . . . . . L | T . . G . . . . . S | . . . . | 10 | H5N1 |

Sequences of M2e from all viruses infecting human in the LANL flu database represented 10 times or more. The number each sequence was found in the database is indicated. Dots represent homology.

TABLE 21

4C2 AND h14C2 SEQUENCE ALIGNMENTS

VH

```
              <------------FWR1------------>  <CDR1>  <-----FWR2--->  <------CDR2----->
14c2          QVQLQQSGPEVVRPGVSVKISCKGSGYIFT   DYAMH   WVKQSHAKSLEWIG  VISTYTGKTNYSQKFKG
62.6 VH1-2    QVQLVQS.A..KK..A...V...A...T..           ..R.APGQG...M.
humanized     QVQLVQSGAEVKKPGASVKVSCKASGYTFT   DYAMH   WVRQAPGQGLEWIG  VISTYTGKTNYSQKFKG <--------------FWR3------------>  <CDR3>        <---FW4--->
14c2          KATMTVDKSSSTAYMELARLTSEDSSVYYCAR  RGDYDAWFAY    WGQGTLVTVSA  (SEQ ID NO: 6)
62.6 VH1-2    RV...R.T.I.......S..R.D.TA......
humanized     RATMTVDKSISTAYMELSRLRSDDTAVYYCAR  RGDYDAWFAY    WGQGTLVTVSS  (SEQ ID NO: 2)
```

VL

```
              <---------FWR1-------->  <------CDR1----->  <------FWR2--->  <-CDR2>
14c2          DIVMSQSPSSLAVSVGEKVSMTC  KSSQRLLYSSDQKNYLA  WYQQKPGQSPKVLIY  WASTRVS
78.2 B3 VK3   ....T...D.....L..RATIN.                     ........P..L...
humanized     DIVMTQSPDSLAVSLGERATMNC  KSSQRLLYSSDQKNYLA  WYQQKPGQPPKVLIY  WASTRVS <-------------FWR3------------->  <--CDR3->    <--FWR4-->
14c2          GVPDRFTGSESGTDFTLTISSVKAEDLAVYYC  QQYYTYPLT    FGAGTKLELK    (SEQ ID NO: 7)
78.2 B3 VK3   ......S..G...........LQ...V.....
humanized     GVPDRFSGSESGTDFTLTISSLQAEDVAVYYC  QQYYTYPLT    FGQGTKVEIK    (SEQ ID NO: 1)
```

The VH and VL sequences of 14C2, the closest human V genes and the humanized sequence are shown. The different parts of the variable region (FWR: framework; CDR: complementarity determining region) are shown. Dots represent homology. Retained murine amino acids are underlined. When the 14C2 VH gene was sequenced (Zhang, et al., 2006), the first seven amino acids, in italics, were not determined and the sequence used here is derived from the M2-80 sequenced VH gene (Zhang, et al., 2006).

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE OF SEQUENCES:

[SEQ ID NO: 1]
AMINO ACID SEQUENCE OF VARIABLE LIGHT CHAIN COMPONENT OF h14C2
DIVMTQSPDSLAVSLGERATMNCKSSQRLLYSSDQKNYLAWYQQKPGQP
PKVLIYWASTRVSGVPDRFSGSESGTDFTLTISSLQAEDVAVYYCQQYY
TYPLTFGQGTKVEIK

-continued

TABLE OF SEQUENCES:

[SEQ ID NO: 2]
AMINO ACID SEQUENCE OF VARIABLE HEAVY CHAIN
COMPONENT OF scFv 25
QVQLVQSGAEVKKPGASVKVSCKASGYTFTDYAMHWVRQAPGQGLEWIG
VISTYTGKTNYSQKFKGRATMTVDKSISTAYMELSRLRSDDTAVYYCAR
RGDYDAWFAYWGQGTLVTVSS

[SEQ ID NO: 3]
NUCLEOTIDE SEQUENCE ENCODING SEQ ID NO 1
GACATCGTTATGACACAAAGCCCAGACAGCCTGGCCGTGAGTCTGGGGGA
GCGTGCCACAATGAACTGCAAGAGTAGCCAGCGCCTGCTGTATTCCTCAG
ACCAAAAAAACTATCTGGCGTGGTATCAGCAGAAACCAGGCCAGCCCCG
AAAGTCCTCATCTACTGGGCCAGCACTCGCGTTTCAGGTGTGCCCGATCG
CTTCAGCGGCAGCGAGAGTGGCACCGATTTCACGCTGACGATCTCCAGCC
TGCAAGCGGAGGACGTTGCGGTCTACTATTGCCAGCAGTATTATACTTAC
CCTCTTACTTTTGGTCAGGGCACCAAAGTTGAAATTAAA

[SEQ ID NO: 4]
NUCLEOTIDE SEQUENCE ENCODING SEQ ID NO 2
CAGGTTCAACTGGTGCAGTCCGGGGCGGAAGTGAAAAAGCCGGGTGCTA
GTGTGAAAGTCAGCTGCAAAGCCAGCGGTTATACGTTTACCGATTACGCC
ATGCATTGGGTGCGGCAGGCCCCCGGCCAAGGCCTTGAATGGATCGGTG
TTATTAGCACTTACACCGGTAAAACGAATTACAGCCAGAAGTTTAAGGGC
CGCGCAACTATGACCGTGGATAAATCTATCTCTACCGCATATATGGAACT
GTCTCGCCTGCGCAGCGATGACACGGCTGTGTATTACTGCGCCCGCCGCG
GAGACTACGATGCATGGTTTGCTTATTGGGGGCAGGGTACTCTGGTTACC
GTATCTAGT

LITERATURE CITED

Barr I. G., Hurt A. C., Deed N., Iannello P., Tomasov C. and Komadina N. (2007) *Antiviral Res*, 75, 173-176.
Bartlett J. G. (2006) *Ann Intern Med*, 145, 141-144.
Beigel J. and Bray M. (2008) *Antiviral Research*, 78, 91-102.
Bright R. A., Medina M. J., Xu X., Perez-Oronoz G., Wallis T. R., Davis X. M., Povinelli L., Cox N. J. and Klimov A. I. (2005) *Lancet*, 366, 1175-1181.
Bright R. A., Shay D. K., Shu B., Cox N. J. and Klimov A. I. (2006) *JAMA*, 295, 891-894.
Carragher D. M., Kaminski D. A., Moquin A., Hartson L. and Randall T. D. (2008) *J Immunol*, 181, 4168-4176.
Carter P., Presta L., Gorman C. M., Ridgway J. B., Henner D., Wong W. L. T., Rowland A. M., Kotts C., M. E. C. and Shepard H. M. (1992) *Proc Natl Acad Sci USA*, 89, 4285-4289.
Chothia C., Novotny J., Bruccoleri R. and Karplus M. (1985) *J Mol Biol*, 186, 651-663.
de Jong M. D., Tran T. T., Truong H. K., Vo M. H., Smith G. J., Nguyen V. C., Bach V. C., Phan T. Q., Do Q. H., Guan Y. et al. (2005) *N Engl J Med*, 353, 2667-2672.
Di Niro R., Sblattero D., Florian F., Stebel M., Zentilin L., Giacca M., Villanacci V., Galletti A., Not T., Ventura A. et al. (2008) *Mol Immunol*, 45, 1782-1791.
Di Niro R., Ziller F., Florian F., Crovella S., Stebel M., Bestagno M., Burrone O., Bradbury A. R., Secco P., Marzari R. et al. (2007) *BMC Biotechnol*, 7, 46-55.
Epstein S. L. (2003) *Expert Rev Anti Infect Ther*, 1, 627-638.
Ernst W. A., Kim H. J., Tumpey T. M., Jansen A. D., Tai W., Cramer D. V., Adler-Moore J. P. and Fujii G. (2006) *Vaccine*, 24, 5158-5168.
Fan J., Liang X., Horton M. S., Perry H. C., Citron M. P., Heidecker G. J., Fu T. M., Joyce J., Przysiecki C. T., Keller P. M. et al. (2004) *Vaccine*, 22, 2993-3003.
Feldman A. M., Lorell B. H. and Reis S. E. (2000) *Circulation*, 102, 272-274.

Feng J., Zhang M., Mozdzanowska K., Zharikova D., Hoff H., Wunner W., Couch R. B. and Gerhard W. (2006) *Virol J*, 3, 102.
Fiers W., De Filette M., Birkett A., Neirynck S, and Min Jou W. (2004) *Virus Research*, 103, 173-176.
Fiore A. E., Shay D. K., Broder K., Iskander J. K., Uyeki T. M., Mootrey G., Bresee J. S, and Cox N. S. (2008) *MMWR Recomm Rep*, 57, 1-60.
Garcia-Rodriguez C., Levy R., Arndt J. W., Forsyth C. M., Razai A., Lou J., Geren I., Stevens R. C. and Marks J. D. (2007) *Nat Biotechnol*, 25, 107-116.
Gillim-Ross L. and Subbarao K. (2007) *PLoS Medicine*, 4, e91.
Govorkova E. A., Leneva I. A., Goloubeva O. G., Bush K. and Webster R. G. (2001) *Antimicrob Agents Chemother*, 45, 2723-2732.
Gubareva L. V., Webster R. G. and Hayden F. G. (2001) *Antimicrob Agents Chemother*, 45, 3403-3408.
Hayden F. G. and Hay A. J. (1992) *Curr Top Microbiol Immunol*, 176, 119-130.
Hoyert D. L., Kung H. C. and Smith B. L. (2005) *Natl Vital Stat Rep*, 53, 1-48.
Hughey P. G., Roberts P. C., Holsinger L. J., Zebedee S. L., Lamb R. A. and Compans R. W. (1995) *Virology*, 212, 411-421.
Hwang W. Y., Almagro J. C., Buss T. N., Tan P. and Foote J. (2005) *Methods*, 36, 35-42.
Jegerlehner A., Schmitz N., Storni T. and Bachmann M. F. (2004) *J Immunol*, 172, 5598-5605.
Jones P. T., Dear P. H., Foote J., Neuberger M. S. and Winter G. (1986) *Nature*, 321, 522-525.
Kettleborough C. A., Saldanha J., Heath V. J., Morrison C. J. and Bendig M. M. (1991) *Protein Eng*, 4, 773-783.
Lackenby A., Hungnes O., Dudman S. G., Meijer A., Paget W. J., Hay A. J. and Zambon M. C. (2008) *Euro Surveill*, 13.
Lonberg N. (2005) *Nat Biotechnol*, 23, 1117-1125.
Macken C., Lu H., Goodman J. and Boykin L. (2001) The value of a database in surveillance and vaccine selection. In Osterhaus A. D. M. E., Cox N. and Hampson A. W. (eds) *Options for the control of influenza*. Elsevier Science, Amsterdam, pp. 103-106.
Marasco W. A. and Sui J. (2007) *Nat Biotechnol*, 25, 1421-1434.
Mariuzza R. A., Jankovic D. L., Boulot G., Amit A. G., Saludjian P., Le Guern A., Mazie J. C. and Poljak R. J. (1983) *J Mol Biol*, 170, 1055-1058.
Matrosovich M., Matrosovich T., Garten W. and Klenk H. D. (2006) *Virol J*, 3, 63.
Morrison S. L., Johnson M. J., Herzenberg L. A. and Oi V. T. (1984) *Proc Natl Acad Sci USA*, 81, 6851-6855.
Moscona A. (2005) *N Engl J Med*, 353, 1363-1373.
Mozdzanowska K., Feng J., Eid M., Kragol G., Cudic M., Otvos L., Jr. and Gerhard W. (2003) *Vaccine*, 21, 2616-2626.
Mozdzanowska K., Maiese K., Furchner M. and Gerhard W. (1999) *Virology*, 254, 138-146.
Neirynck S., Deroo T., Saelens X., Vanlandschoot P., Jou W. M. and Fiers W. (1999) *Nat Med*, 5, 1157-1163.
Okuda K., Ihata A., Watabe S., Okada E., Yamakawa T., Hamajima K., Yang J., Ishii N., Nakazawa M., Okuda K. et al. (2001) *Vaccine*, 19, 3681-3691.
Palese P., Shaw, M. L. (2006) Orthomyxoviridae: the viruses and Their Replication. In Knipe D. M., Howley, P. M., Griffin, D. M., Lamb, R. A., Martin, M. A. (ed) *Fields Virology*. Lippincott, Williams, & Wilkins, Philadelphia, pp. 1647-1689.

Pedersen J. T., Henry A. H., Searle S. J., Guild B. C., Roguska M. and Rees A. R. (1994) *J Mol Biol*, 235, 959-973.

Podewils L. J., Liedtke L. A., McDonald L. C., Hageman J. C., Strausbaugh L. J., Fischer T. K., Jernigan D. B., Uyeki T. M. and Kuehnert M. J. (2005) *Clin Infect Dis*, 40, 1693-1696.

Razai A., Garcia-Rodriguez C., Lou J., Geren I. N., Forsyth C. M., Robles Y., Tsai R., Smith T. J., Smith L. A., Siegel R. W. et al. (2005) *J Mol Biol*, 351, 158-169.

Reichert J. M. and Dewitz M. C. (2006) *Nat Rev Drug Discov*, 5, 191-195.

Reichert J. M., Rosensweig C. J., Faden L. B. and Dewitz M. C. (2005) *Nat Biotechnol*, 23, 1073-1078.

Roguska M. A., Pedersen J. T., Keddy C. A., Henry A. H., Searle S. J., Lambert J. M., Goldmacher V. S., Blattler W. A., Rees A. R. and Guild B. C. (1994) *Proc Natl Acad Sci USA*, 91, 969-973.

Routledge E. G., Lloyd I., Gorman S. D., Clark M. and Waldmann H. (1991) *Eur J Immunol*, 21, 2717-2725.

Sblattero D. and Bradbury A. (2000) *Nat Biotechnol*, 18, 75-80.

Schnell J. R. and Chou J. J. (2008) *Nature*, 451, 591-595.

Simmons C. P., Bernasconi N. L., Suguitan A. L., Mills K., Ward J. M., Chau N. V., Hien T. T., Sallusto F., Ha do Q., Farrar J. et al. (2007) *PLoS Med*, 4, e178.

Slepushkin V. A., Katz J. M., Black R. A., Gamble W. C., Rota P. A. and Cox N. J. (1995) *Vaccine*, 13, 1399-1402.

Stouffer A. L., Acharya R., Salom D., Levine A. S., Di Costanzo L., Soto C. S., Tereshko V., Nanda V., Stayrook S, and DeGrado W. F. (2008) *Nature*, 451, 596-599.

Studnicka G. M., Soares S., Better M., Williams R. E., Nadell R. and Horwitz A. H. (1994) *Protein Eng*, 7, 805-814.

Tompkins S. M., Zhao Z. S., Lo C. Y., Misplon J. A., Liu T., Ye Z., Hogan R. J., Wu Z., Benton K. A., Tumpey T. M. et al. (2007) *Emerg Infect Dis*, 13, 426-435.

Treanor J. J., Tierney E. L., Zebedee S. L., Lamb R. A. and Murphy B. R. (1990) *J Virol*, 64, 1375-1377.

Tripp R. A. and Tompkins S. M. (2008) *Curr Opin Investig Drugs*, 9, 836-845.

Tsurushita N., Hinton P. R. and Kumar S. (2005) *Methods*, 36, 69-83.

Ulmer J. B., Donnelly J. J., Parker S. E., Rhodes G. H., Feigner P. L., Dwarki V. J., Gromkowski S. H., Deck R. R., DeWitt C. M., Friedman A. et al. (1993) *Science*, 259, 1745-1749.

Vargas-Madrazo E. and Paz-Garcia E. (2003) *J Mol Recognit*, 16, 113-120.

Wang R., Song A., Levin J., Dennis D., Zhang N. J., Yoshida H., Koriazova L., Madura L., Shapiro L., Matsumoto A. et al. (2008) *Antiviral Res*.

Watabe S., Xin K. Q., Ihata A., Liu L. J., Honsho A., Aoki I., Hamajima K., Wahren B. and Okuda K. (2001) *Vaccine*, 19, 4434-4444.

Winter G., Griffiths A. D., Hawkins R. E. and Hoogenboom H. R. (1994) *Annu Rev Immunol*, 12, 433-455.

Wright P. F., Neumann, G., Kawaoka, Y. (2006) Orthothomyxoviruses. In Knipe D. M., Howley, P. M., Griffin, D. M., Lamb, R. A., Martin, M. A. (ed) *Fields Virology*. Lippincott, Williams, & Wilkins, Philadelphia, pp. 1691-1740.

Zebedee S. L. and Lamb R. A. (1988) *J Virol*, 62, 2762-2772.

Zeitlin L., Cone R. A., Moench T. R. and Whaley K. J. (2000) *Microbes Infect*, 2, 701-708.

Zhang M., Zharikova D., Mozdzanowska K., Otvos L. and Gerhard W. (2006) *Mol Immunol*, 43, 2195-2206.

Zharikova D., Mozdzanowska K., Feng J., Zhang M. and Gerhard W. (2005) *J Virol*, 79, 6644-6654.

---

The invention claimed is:

1. An isolated polynucleotide encoding an anti-M2e monoclonal antibody, or antigen-binding fragment thereof, wherein the antibody or the antigen-binding fragment thereof specifically binds influenza M2e polypeptide, and wherein the polynucleotide encodes a light chain variable region of SEQ ID NO: 1 and a heavy chain variable region of SEQ ID NO: 2 of the antibody or antigen binding fragment thereof.

2. The isolated polynucleotide of claim 1, wherein the antibody is a scFv.

3. The isolated polynucleotide of claim 1, wherein the antigen-binding fragment is selected from the group consisting of Fab and Fab'.

4. The isolated polynucleotide of claim 1, wherein the antibody is a minibody.

5. The isolated polynucleotide of claim 1, wherein the antibody is an immunoglobulin selected from the group consisting of IgA, IgD, IgE, IgG and IgM.

6. The isolated polynucleotide of claim 1, comprising SEQ ID NO: 3 and SEQ ID NO: 4.

7. A vector comprising the polynucleotide of claim 1.

8. The vector of claim 7, wherein the vector is a plasmid vector.

9. The vector of claim 7, wherein the vector is a phage vector.

10. An isolated host cell comprising the vector of claim 7.

* * * * *